US011781079B2

United States Patent
Höfel et al.

(10) Patent No.: US 11,781,079 B2
(45) Date of Patent: Oct. 10, 2023

(54) PROCESS FOR SEPARATING A COMPONENT MIXTURE AND SEPARATION APPARATUS

(71) Applicant: LINDE GmbH, Pullach (DE)

(72) Inventors: Torben Höfel, Munich (DE); Duc Tuat Pham, Penzberg (DE)

(73) Assignee: LINDE GmbH, Pullach (DE)

( * ) Notice: Subject to any disclaimer, the term of this patent is extended or adjusted under 35 U.S.C. 154(b) by 428 days.

(21) Appl. No.: 17/044,796

(22) PCT Filed: Apr. 5, 2019

(86) PCT No.: PCT/EP2019/058716
§ 371 (c)(1),
(2) Date: Oct. 1, 2020

(87) PCT Pub. No.: WO2019/193187
PCT Pub. Date: Oct. 10, 2019

(65) Prior Publication Data
US 2021/0139797 A1   May 13, 2021

(30) Foreign Application Priority Data
Apr. 6, 2018 (EP) .................... 18166161

(51) Int. Cl.
*C10G 70/04* (2006.01)
*C10G 47/00* (2006.01)
(Continued)

(52) U.S. Cl.
CPC ........... *C10G 70/041* (2013.01); *B01D 3/143* (2013.01); *B01D 3/4294* (2013.01); *C10G 47/00* (2013.01); *C10G 2300/1081* (2013.01)

(58) Field of Classification Search
CPC .......... C10G 70/40; C10G 47/00; B01D 3/14; B01D 3/42
See application file for complete search history.

(56) References Cited

U.S. PATENT DOCUMENTS

| 4,157,905 A | 6/1979 | Hengstebeck |
| 2013/0102827 A1* | 4/2013 | Simon .................. C10G 70/043 422/119 |

FOREIGN PATENT DOCUMENTS

| CN | 103449950 B | 4/2015 |
| DE | 102005050388 A1 | 4/2007 |

(Continued)

OTHER PUBLICATIONS

WO 2007/045364 A2_English (Year: 2007).*
(Continued)

*Primary Examiner* — Youngsul Jeong
(74) *Attorney, Agent, or Firm* — Cozen O'Connor

(57) ABSTRACT

A process for separating a component mixture comprising essentially hydrocarbons having two or two or more carbon atoms, methane and hydrogen using a distillation apparatus (10) is proposed. Fluid (a, c, e, g, i) from the component mixture is cooled stepwise to a first pressure level, with separation of first condensates (b, d, f, h, j) out of the fluid (a, c, e, g, i) in each case. Fluid (k) from the component mixture that remains in gaseous form thereafter is expanded to a second pressure level in an expander, giving a second condensate (l). Fluid from the first condensates (b, d, f, h, j) is expanded from the first pressure level to the second pressure level and fed together with the fluid from the second condensates into the distillation apparatus (10) which is being operated at the second pressure level. The present invention likewise provides a corresponding separation apparatus.

13 Claims, 4 Drawing Sheets

(51) Int. Cl.
    *B01D 3/14*        (2006.01)
    *B01D 3/42*        (2006.01)

(56) References Cited

FOREIGN PATENT DOCUMENTS

| FR | 2957931 A1 | 9/2011 | | |
|---|---|---|---|---|
| JP | S61189233 A | 8/1986 | | |
| WO | WO-2007045364 A2 * | 4/2007 | ............... | C07C 7/09 |

OTHER PUBLICATIONS

Eurasian Patent Application No. 202092067 Office Action dated Jan. 25, 2022, with English translation; 4 pages.
PCT/EP2019/058716 International Search Report and Written Opinion dated Jun. 19, 2019; 10 pages.
GC Application No. 2019-37312 Examination Report dated Oct. 21, 2021, 4 pages.
Indonesian Patent Application No. INP00202008328, Office Action with English translation, dated Aug. 2, 2022, 5 pages.

* cited by examiner

PROCESS FOR SEPARATING A COMPONENT MIXTURE AND SEPARATION APPARATUS

The present invention relates to a process for separating a component mixture comprising essentially hydrocarbons having two or two or more carbon atoms, methane and hydrogen, and to a separation apparatus according to the preamble of the independent claims.

STATE OF THE ART

Processes and apparatuses for steamcracking of hydrocarbons are known and are described, for example, in the article "Ethylene" in Ullmann's Encyclopedia of Industrial Chemistry, online since 15 Apr. 2007, DOI 10.1002/14356007.a10_045.pub2. By steamcracking, but also using other processes and apparatuses, component mixtures are obtained in the form of what are called crude gases or cracked gases which, after processing comprising the removal of water and carbon dioxide and of oil- or gasoline-like components, are separated at least partly into the components present in each case. This can be effected in different ways.

The present invention can be used for removal of methane and hydrogen from a component mixture comprising essentially hydrocarbons having two carbon atoms, methane and hydrogen, but also low in or free of heavier hydrocarbons, and is described hereinafter particularly with reference to this variant. A component mixture of this kind is obtained in the separation sequences known from the cited literature particularly in a deethanization of the processed cracked gas when this deethanization occurs first in the separation process. As elucidated once again below, a component mixture of this kind or a corresponding stream of matter is typically also referred to as "C2minus stream".

However, the present invention can also be used for removal of methane and hydrogen from a component mixture comprising essentially hydrocarbons having two and more carbon atoms, methane and hydrogen. A component mixture of this kind may especially be in the form of the cracked gas that has been processed as elucidated but is yet to be treated further by separation processes.

In both cases, i.e. the removal of methane and hydrogen from a component mixture comprising essentially hydrocarbons having two carbon atoms, methane and hydrogen, but low in or free of heavier hydrocarbons, and the removal of methane and hydrogen from a component mixture comprising essentially hydrocarbons having two or more carbon atoms, methane and hydrogen, what is called a demethanization is thus undertaken in the context of the present invention. This occurs second in a corresponding separation sequence in the first case, and first in the latter case.

Conventional processes, for example a process as illustrated in FIG. 1, comprise cooling down a C2minus stream stepwise under pressure in heat exchangers and separating out liquid condensates in each case downstream of these heat exchangers. A fraction of the C2minus stream originally fed in that remains in gaseous form at a pressure of about 30 bar abs. and a temperature of below about −100° C. is expanded in an expander. The fraction expanded in the expander and the condensates separated out of the C2minus stream beforehand are fed into a rectification column (called a demethanizer) at different heights.

In the bottom of the rectification column, a liquid bottom product including essentially hydrocarbons having two carbon atoms is formed and drawn off. A gaseous top product comprising essentially methane and hydrogen is drawn off from the top of the rectification column as top stream and cooled down to about −160° C. by expanding in an expander.

The expanded top stream is used for cooling and at least partial liquefaction of a first gaseous stream of matter from the rectification column in a first plate exchanger and of a second gaseous stream of matter in a second plate exchanger. The rectification column used is in two-part form and the gaseous streams of matter that have been at least partly liquefied in each case are used as return stream to the two parts of the rectification column. Subsequently, the expanded top stream is used to cool down the C2minus stream and hence used in the formation of the condensates.

A corresponding process is also disclosed in DE 10 2005 050 388 A1. Also FR 2 957 931 A1 and JP S61 189233 A show processes for the treatment of gas mixtures from steam cracking processes.

A disadvantage of the process elucidated is that the plate exchangers mentioned that are used for cooling and at least partial liquefaction of the first gaseous stream of matter and the second gaseous stream of matter from the rectification column must be disposed above the rectification column in order that these streams of matter or the liquefied fractions can flow back to the rectification column as return stream. The expanded top stream with a certain fraction of liquid owing to the expansion has to be transported back to these plate exchangers in a complex manner. The use of this expanded top stream as coolant in the plate exchangers at a great height is associated with technical difficulties since liquid phase and gas phase are preferably guided separately into the plate exchangers and a small pressure drop can be tolerated.

The installation of the plate exchangers at the top of the rectification column, in summary, is inconvenient and costly. The same is also true of a comparable demethanization of a component mixture comprising not only hydrocarbons having two carbon atoms but additionally heavier hydrocarbons. The problem addressed by the invention is therefore that of remedying these disadvantages of the prior art.

DISCLOSURE OF THE INVENTION

Against that background, the invention proposes a process for separating a component mixture comprising essentially hydrocarbons having two or two or more carbon atoms, methane and hydrogen, and a corresponding separation apparatus having the respective features of the independent claims. Preferred configurations are the subject of the dependent claims and of the description which follows.

Before the features and advantages of the present invention are elucidated, the basics thereof and the terms used will be elucidated.

The present invention is especially used for separation of component mixtures that are obtained by steamcracking processes. However, it is not restricted to these. The component mixture comprising essentially hydrocarbons having two or two or more carbon atoms, methane and hydrogen, if it is produced using a steamcracking process, is formed as a fraction of a "cracked gas" obtained in the steamcracking process. For this purpose, a corresponding cracked gas is typically freed of water, acid gases and oil- and gasoline-type components, and compressed as already elucidated. It then constitutes the component mixture comprising essentially hydrocarbons having two or more carbon atoms, methane and hydrogen. The component mixture comprising essentially hydrocarbons having two carbon atoms, methane and hydrogen can in turn be formed therefrom by removing hydrocarbons having three or possibly more carbon atoms, especially by means of rectification. Either the component mixture comprising essentially hydrocarbons having two or more carbon atoms, methane and hydrogen or the component mixture comprising essentially hydrocarbons having two carbon atoms, methane and hydrogen can be processed ("demethanized") in the context of the present invention.

Standard processes include the separation of the cracked gas into a number of fractions based on the different boiling points of the components present. These are referred to in the art by abbreviations indicating the carbon number of the hydrocarbons predominantly or exclusively present in each case. Thus a "C1 fraction" is a fraction containing predominantly or exclusively methane (but by convention in some cases also hydrogen, then also referred to as "C1minus fraction"). By contrast a "C2 fraction" contains predominantly or exclusively ethane, ethylene and/or acetylene. A "C3 fraction" contains predominantly propane, propylene, methylacetylene and/or propadiene. A "C4 fraction" contains predominantly or exclusively butane, butene, butadiene and/or butyne, wherein the respective isomers may be present in different proportions depending on the source of the C4 fraction. The same applies correspondingly for the "C5 fraction" and the higher fractions. Multiple fractions of this kind may also be combined in terms of process and/or designation. For example a "C2plus fraction" contains predominantly or exclusively hydrocarbons having two or more carbon atoms and a "C2minus fraction" contains predominantly or exclusively hydrocarbons having one or two carbon atoms.

In the terminology used here, component mixtures may be rich or poor in one or more components, wherein "rich" may represent a content of at least 90%, 95%, 99%, 99.5%, 99.9%, 99.99% or 99.999% and "poor" may represent a content of not more than 10%, 5%, 1%, 0.1%, 0.01% or 0.001% on a molar, weight or volume basis. In the terminology used here, component mixtures may also be enriched or depleted of one or more components, where these terms relate to a content in another component mixture from which the component mixture in question has been obtained. The component mixture is "enriched" when it contains not less than 1.1 times, 1.5 times, 2 times, 5 times, 10 times, 100 times or 1000 times the content, and "depleted" when it contains not more than 0.9 times, 0.5 times, 0.1 times, 0.01 times or 0.001 times the content of a component, based on the other component mixture. If it is said here that a component mixture contains "essentially" one or more components, this is especially understood to mean that the component mixture is at least rich in the one or more components in the above-elucidated sense or includes exclusively the one or more components.

A component mixture is "derived" from another component mixture when it includes at least some components present in or obtained from the other component mixture. A component mixture derived in this way may be obtained from another component mixture by separating off or branching off a portion or one or more components, enriching or depleting with regard to one or more components, chemically or physically converting one or more components, heating, cooling, pressurizing and the like.

The terms "pressure level" and "temperature level" are used in the present application to characterize pressures and temperatures, these being intended to express the fact that corresponding pressures and temperatures need not be used in the form of exact pressure/temperature values. However, such pressures and temperatures typically vary within particular ranges of, for example, ±1% or 10% around an average value. Corresponding pressure levels and temperature levels may lie in disjoint ranges or in overlapping ranges. More particularly, pressure levels include slightly different pressures that arise owing to unavoidable or expected pressure drops. The same holds for temperature levels. The pressure levels indicated here in bar are absolute pressures.

A "heat exchanger" serves for indirect transfer of heat between at least two streams of matter being conducted, for example, in countercurrent to one another, for example a warmer gaseous stream of matter and one or more colder liquid streams of matter. A heat exchanger may be formed from a single heat exchanger section or a plurality of parallel- and/or series-connected heat exchanger sections, for example from one or more plate heat exchanger blocks. A heat exchanger has "passages" formed as separate fluid channels with heat exchange surfaces.

A "liquid separator" or "separation vessel" is a vessel in which a liquid, called condensate, is separated out of a gaseous stream of matter or a biphasic stream (which is partly in liquid form and partly in gaseous form). The condensate can be removed at least partly in gaseous form from the liquid separator (typically from an upper region, "top").

In the terminology used here, a "rectification column" is a separation unit set up for at least partial fractionation of a component mixture (fluid) provided in gaseous or liquid form or in the form of a biphasic mixture having liquid and gaseous components, possibly even in the supercritical state, i.e. for producing pure substances or component mixtures in each case from the component mixture that are enriched/depleted or rich/poor with regard to at least one component compared to the component mixture in the sense elucidated above. Rectification columns are sufficiently well known from the field of separation technology. Rectification columns typically take the form of cylindrical metal vessels equipped with internals, for example sieve trays or ordered and unordered packings. One feature of a rectification column is that a liquid fraction separates out in its lower region, also referred to as the bottom. This liquid fraction, which is referred to here as bottoms liquid, is heated in a rectification column by means of a reboiler, such that a portion of the bottoms liquid is evaporated continuously and ascends in gaseous form in the rectification column. A rectification column is also typically provided with what is called a tops condenser into which at least a portion of a gas mixture which accumulates in an upper region of the rectification column or a corresponding pure gas, referred to here as tops gas, is fed, is liquefied in part to give a condensate and is applied as liquid return stream at the top of the rectification column. A portion of the condensate obtained from the tops gas can be used in some other way. With regard to the design and specific configuration of rectification columns, reference is made to relevant textbooks (see, for example, Sattler, K: Thermische Trennverfahren: Grundlagen, Auslegung, Apparate [Thermal Separation Processes: Basics, Design, Apparatuses], 3rd edition 2001, Weinheim; Wiley-VCH).

In the terminology being used here, a "distillation apparatus" is a separation apparatus having at least two different distillation units. A distillation apparatus may, for example, be a rectification column or comprise components as typical of a rectification column. A distillation apparatus may also take the form of a rectification column having two sections separated from one another by means of a tray, where liquid accumulates on the tray and flows over a weir into the section beneath and hence forms a return stream to the section beneath. Liquid exchange is also possible via conduits.

Advantages of the Invention

The present invention proceeds from a process, known in this respect, for separation of a component mixture including essentially hydrocarbons having two or two or more carbon atoms, and methane and hydrogen. As elucidated above, a component mixture of this kind may take the form of a cracked gas that has been processed but not yet subjected to separation processes, or else of a C2minus fraction. A process of this kind is conducted using a distillation apparatus in which a stream of matter comprising methane and hydrogen is separated from a heavier fraction, i.e. a component mixture including essentially hydrocarbons having two or two or more carbon atoms and a component mixture including essentially methane and hydrogen are formed.

In such a process, fluid from the component mixture at a first pressure level is cooled down stepwise from a first temperature level via two or more intermediate temperature levels to a second temperature level. At each of the intermediate temperature levels, condensates are separated out of the fluid at the first pressure level, i.e. without expansion in each case.

If it is stated here that "fluid from a stream of matter" or "fluid from a component mixture" is treated in any way, what this means is, for example, that the entire fluid, a fluid derived from a starting fluid or a substream of a stream of matter that has been formed from a corresponding fluid is used. More particularly, in the process step elucidated above, a condensate and a fraction that remains in gaseous form are formed in each case from a corresponding fluid. The fraction that remains in gaseous form is cooled down in each case to a next lowest temperature level (i.e. the intermediate temperature levels or ultimately the second temperature level).

Fluid from the component mixture that remains in gaseous form at the second temperature level, i.e. the fluid which is not separated out in the form of the respective condensates, is fed into an expander at the first pressure level and expanded to a second pressure level, where the expansion results in cooling and partial condensation and hence forms a biphasic stream comprising a liquid and a gaseous portion.

The condensates formed by the cooling to the intermediate temperature levels and the second temperature level and the biphasic stream are each fed at least partly into a distillation apparatus which is being operated at the second pressure level, where at least one liquid stream of matter comprising essentially hydrocarbons having two or two or more carbon atoms and a gaseous stream of matter comprising essentially methane and hydrogen are obtained in the distillation apparatus and are drawn off from the distillation apparatus.

In the process, fluid from the condensates formed by the cooling to the intermediate temperature levels and the second temperature level and from the biphasic stream are each expanded from the first pressure level to a second pressure level below the first pressure level and fed into the distillation apparatus which is being operated at the second pressure level.

According to the invention, the second temperature level mentioned is −125 to −150° C., especially about −145° C. This is well below corresponding temperature levels as used in processes according to the prior art in the cooling of corresponding feed mixtures. Reference is made to the example of FIG. 1. Owing to the subsequent decompression, the temperature level is distinctly decreased once again, in the example from about −145° C. especially to about −162° C.

According to the invention, the distillation apparatus comprises a first distillation unit and a second distillation unit, wherein the first distillation unit is operated with a third temperature level at its top which is below the second temperature level, and wherein the second distillation unit is operated with a fourth temperature level at its top which is above the second temperature level. The liquid part of the biphasic stream is fed into the first distillation unit at least in part. However, this does not exclude the possibility that the gaseous part of the biphasic stream can also be fed at least partly into the first distillation unit. On the one hand, the liquid part of the biphasic stream is used as a reflux. A further effect, however, is that the cold temperature of the expanded biphasic stream (e.g. approx. −162° C.) produces even more liquid from the rising gas stream of the first separation unit. This happens because the temperature level of the biphasic stream after expansion is even lower than the third temperature level at the top of the column (e.g. approx. −152° C.). The mentioned direct and indirect effects can equally contribute to the reflux formation.

In particular, the liquid part of the biphasic stream or a corresponding partial quantity thereof is fed into an upper region close to the top of the first distillation unit or at its top, a region close to the top representing in particular a region without trays and/or packings which is located directly below an upper closure of the first distillation unit. The "head" means the uppermost part of a distillation unit above which the corresponding distillation unit has no further separating trays or packings.

Preferably, in the context of this invention, the first distillation unit is operated without a reflux which is formed by fluid withdrawn in gaseous form from the first distillation unit. In other words, the first distillation unit is advantageously operated without a head condenser. The second distillation unit, which may in particular be located geodetically below the first distillation unit, is operated in particular with a head condenser, which may also be located geodetically above the first distillation unit. The assignment of a head condenser to a distillation unit results from the fluid or head gas treated there, but not from the arrangement.

The liquid stream of matter including essentially hydrocarbons having two or two or more carbon atoms is drawn off from the bottom of the second distillation unit, and the gaseous stream of matter including essentially methane and hydrogen at the top of the first distillation unit.

The third temperature level below the second temperature level at the top of the first distillation unit especially results from the feeding of the fluid that has been cooled down to the second temperature level and then expanded, i.e. the biphasic stream. Advantageously, no gaseous fluid which is recycled to the first distillation unit as a return stream in liquefied form is withdrawn from the first distillation unit; instead, all fluid fed into the first distillation unit in liquid form is provided exclusively in the form of the condensates formed by the cooling to the intermediate temperature levels and the second temperature level and/or in the form of a liquid fraction of the biphasic stream or portions of each.

The operation of the first distillation unit with the third temperature level at the top and the feeding particularly of the biphasic stream into the first distillation unit or the liquid reflux to this means that it is possible to obtain a top stream essentially free of hydrocarbons having two carbon atoms therefrom, namely the gaseous stream of matter already mentioned that includes essentially methane and hydrogen, without having to form a reflux of tops gas by means of separate heat exchangers that are especially disposed above the top of the rectification column as in the prior art for the purpose.

The fourth temperature level above the second temperature level at the top of the second distillation unit is especially achieved by the temperatures of the condensates fed into the distillation apparatus, which are obtained by the cooling to the intermediate temperature levels and the second temperature level. The operation at a correspondingly higher temperature level which is also above a corresponding temperature level according to the prior art allows a return stream to the second distillation unit to be formed without any requirement for significant cooling as in the prior art for the purpose. Instead, it is possible to resort to known coolants such as ethylene for the purpose. An ethylene coolant circuit is present in any case in a corresponding plant for cooling of the feed mixture, as already elucidated.

In the context of the present invention, a gaseous stream of matter to be recycled is thus withdrawn as in the prior art from the distillation apparatus, but only from the second distillation unit mentioned, fed into a condenser, cooled down in the condenser and liquefied, and applied to the distillation apparatus or the second distillation unit thereof as return stream. However, the condenser is operated at a temperature level above the second temperature level. The distillation apparatus thus advantageously has a condenser which is operated at such a temperature level.

The use of the measures of the invention avoids the need, as in the prior art, to cool a first gaseous stream of matter from the rectification column in a first plate exchanger and a second gaseous stream of matter in a second heat exchanger to very low temperatures and liquefy them in order to be able to provide a return stream to the rectification column. By contrast with the known process, the present invention thus makes it possible to dispense with the two plate exchangers at the top of the rectification column in which, conventionally, virtually the entire C1minus fraction is used as coolant and which has to be transported in a complex manner to the plate exchangers.

According to the invention, the third temperature level mentioned is −150 to −170° C., especially about −162° C. This is well below temperature levels as used in processes according to the prior art in the cooling of corresponding feed mixtures. Reference is made to the example of FIG. 1. The fourth temperature level mentioned is −50 to −130° C. The same is true of the temperature level in the condenser mentioned. The first pressure level is especially 25 to 30 bar, the second pressure level 10 to 15 bar.

The use of the solution according to the invention leaves the mass balance and heat balance of a corresponding system virtually unchanged, and does not entail any further influence on the overall process. The invention enables a reduction in the capital costs and simplification in the installation of the plant.

Advantageously, fluid from the gaseous stream of matter drawn off from the distillation apparatus, including essentially methane and hydrogen, i.e. tops gas from the distillation apparatus or from the first distillation unit of the distillation apparatus, is used at least for cooling of the fluid from the hydrocarbon mixture from the first temperature level via the intermediate temperature levels to the second temperature level. This enables efficient cooling of corresponding fluid. In this case, in particular, further expansion can be effected in order to obtain the low temperatures required. The gaseous stream of matter drawn off from the distillation apparatus is withdrawn therefrom, for example, at −150 to −160° C., especially about −153° C. A corresponding temperature level here is also referred to as the fifth temperature level.

One of the intermediate temperature levels is advantageously −120 to −125° C., and one of the intermediate temperature levels −140 to −145° C. The cold tops gas from the fifth temperature level is advantageously used to cool down a fraction of the component mixture that has remained in gaseous form in an upstream condensation from the intermediate temperature level at −120 to −125° C. to the intermediate temperature level at −140 to −145° C., with heating of the tops gas to a temperature level of −120 to −130° C., for example about −126° C. Subsequently, the tops gas is advantageously cooled down in an expander to a temperature level of −150 to −160° C., for example about −157° C., and used for cooling in respective upstream condensations of fractions of the component mixture that have remained in gaseous form to intermediate temperature levels of, for example, −120 to −125° C., −95 to −100° C., −74 to −79° C. and −48 to −53° C. In addition, ethylene coolant is used in order to undertake corresponding cooling to the intermediate temperature levels.

Advantageously, the bottoms liquid from the first separation unit is collected and guided to the second separation unit in order to serve as return stream or as cooling in the second separation unit.

The process according to the invention is particularly suitable for separation of a component mixture which is obtained from a cracked gas obtained by means of a steam-cracking process.

The invention likewise provides a corresponding separation apparatus. The separation apparatus is set up to separate a component mixture including essentially hydrocarbons having two or two or more carbon atoms and methane, and hydrogen and has a distillation apparatus, a condenser and at least one expander. With regard to the further constituents of a corresponding plant, reference is made to the above elucidations.

The invention and embodiments of the invention are more particularly elucidated with reference to the appended drawings.

DETAILED DESCRIPTION OF THE DRAWINGS

In the figures, corresponding elements bear identical reference signs and, for the sake of clarity, are not elucidated repeatedly. In the figures which follow, the invention is described with reference to a separating treatment of a component mixture including essentially hydrocarbons having two carbon atoms and methane and hydrogen. However, it is suitable in the same way for separating treatment of a component mixture including essentially hydrocarbons having two or more carbon atoms and methane and hydrogen.

Figure 1:
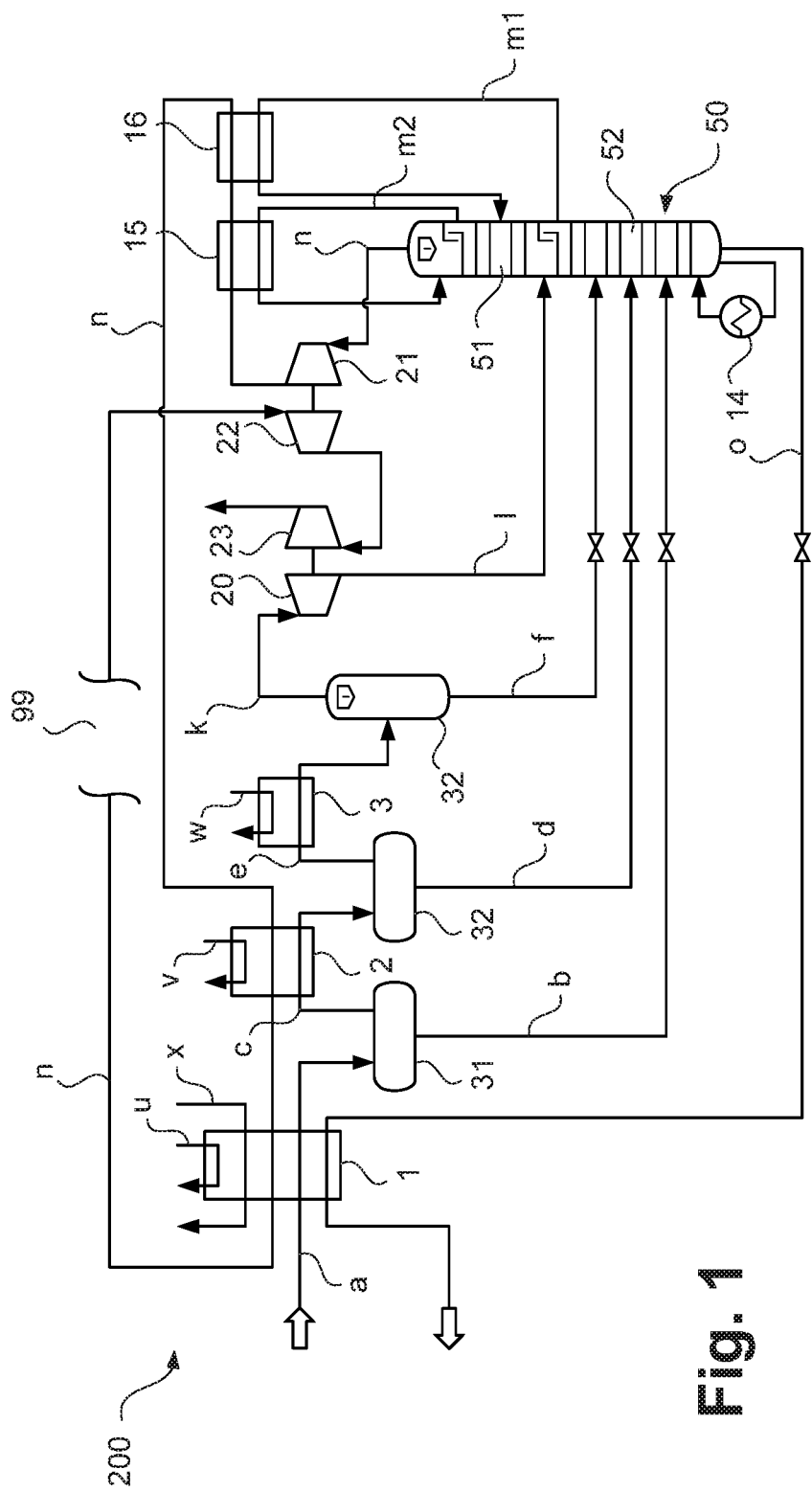
FIG. 1 shows a separation apparatus for separation of a component mixture according to the prior art.

FIG. 1 shows a separation apparatus for separation of a component mixture in a non-inventive embodiment. The separation apparatus is collectively labelled 200 and is set up to separate a component mixture including essentially hydrocarbons having two carbon atoms, methane and hydrogen (i.e. a C2minus fraction). The C2minus fraction is fed to the separation apparatus 200 in the form of a stream of matter a.

The separation apparatus 200 comprises a first heat exchanger 1, a second heat exchanger 2 and a third heat exchanger 3. Stream of matter a is first guided through the first heat exchanger 1 and cooled therein. It is subsequently fed into a first liquid separator 31. The cooling in the first heat exchanger 1 is effected by separating out a liquid condensate in the first liquid separator 31. This is drawn off at the base of the first liquid separator 31 as stream of matter b. The further use of stream of matter b is elucidated below.

A fraction of stream of matter a that has remained in gaseous form in the first liquid separator 31 is guided as stream of matter c through the second heat exchanger 2 and then fed into a second liquid separator 32. In the latter as well, a liquid condensate separates out at the base and is drawn off in the form of stream of matter d. A fraction of stream of matter c that has still remained in gaseous form is guided as stream of matter e through a third heat exchanger 3 and then fed into a third liquid separator 33. In the latter as well, a liquid condensate separates out at the base and is drawn off in the form of stream of matter f. A fraction of stream of matter e that has still remained in gaseous form is guided into an expander 20 as stream of matter k, expanded and at least partly liquefied. A biphasic stream formed in this way is provided in the form of a stream of matter l.

The separation apparatus 200 further comprises a rectification column 50 which is operated with a reboiler 14 which is not elucidated any further, the heat exchanger of which is operated, for example, with a propylene stream that comes from other plant components. Also assigned to the rectification column 50 are two plate exchangers 15, 16, the operation of which is elucidated below. The rectification column 50 has two sections 51, 52.

Owing to the successive cooling of streams of matter a, c, e and k, the condensates obtained correspondingly, which are obtained in the form of streams of matter b, d, f, l, have different contents of hydrocarbons having two carbon atoms, methane and hydrogen. More particularly, stream of matter l has a higher methane and hydrogen content than stream of matter f, stream of matter f has a higher methane and hydrogen content than stream of matter d, and stream of matter d has a higher methane and hydrogen content than stream of matter b.

Streams of matter b, d, f and l are therefore fed into the rectification column 50 at different heights, which has application devices suitable for the purpose between the trays, which are shown here in highly schematic form.

A gaseous stream of matter n is drawn off from the top of rectification column 50 and expanded in an expander 21 and significantly cooled or at least partly liquefied as a result. Stream of matter n comprises predominantly methane and hydrogen (it is thus a "C1minus" fraction). The liquefied stream of matter n is guided through the two plate exchangers 15, 16 and used for cooling therein. Subsequently, stream of matter n is guided through heat exchanger 2 and used for cooling of gaseous stream of matter c, and guided through heat exchanger 1 and used for cooling of gaseous stream of matter a. Subsequently, stream of matter n, especially after use in a preliminary cooling unit 99, is guided through two boosters 22, 23 coupled to the expanders 20 and 21, and discharged from the plant as tail gas.

In the bottom of rectification column 50, a liquid condensate separates out, essentially consisting of hydrocarbons having two carbon atoms (this is a "C2" fraction). The condensate is drawn off in the form of stream of matter o, heated in the first heat exchanger 1 and then, for example, sent to a further separation apparatus such as a C2 splitter.

A gaseous stream of matter m1 is withdrawn in gaseous form from rectification column 50 at a first position, cooled down in the plate exchanger 16 and hence at least partly liquefied and sent to rectification column 50 as return stream at a second position, i.e. guided back into rectification column 50 by gravity. A further gaseous stream of matter m2 is withdrawn in gaseous form from rectification column 50 at a third position, cooled down in the plate exchanger 15 and hence at least partly liquefied and sent to rectification column 50 as return stream at a fourth position, i.e. guided back into rectification column 50 by gravity, where the first position is below the second position, the second position is below the third position and the third position is below the fourth position. As mentioned above, in plate exchangers 15, 16, the liquefied stream of matter n is used for cooling of streams of matter m1 and m2, and has to be transported in a complex manner to the plate exchangers that are at a great height. The installation of these plate exchangers 15, 16 at the top of rectification column 50 is inconvenient and costly.

Figure 2:
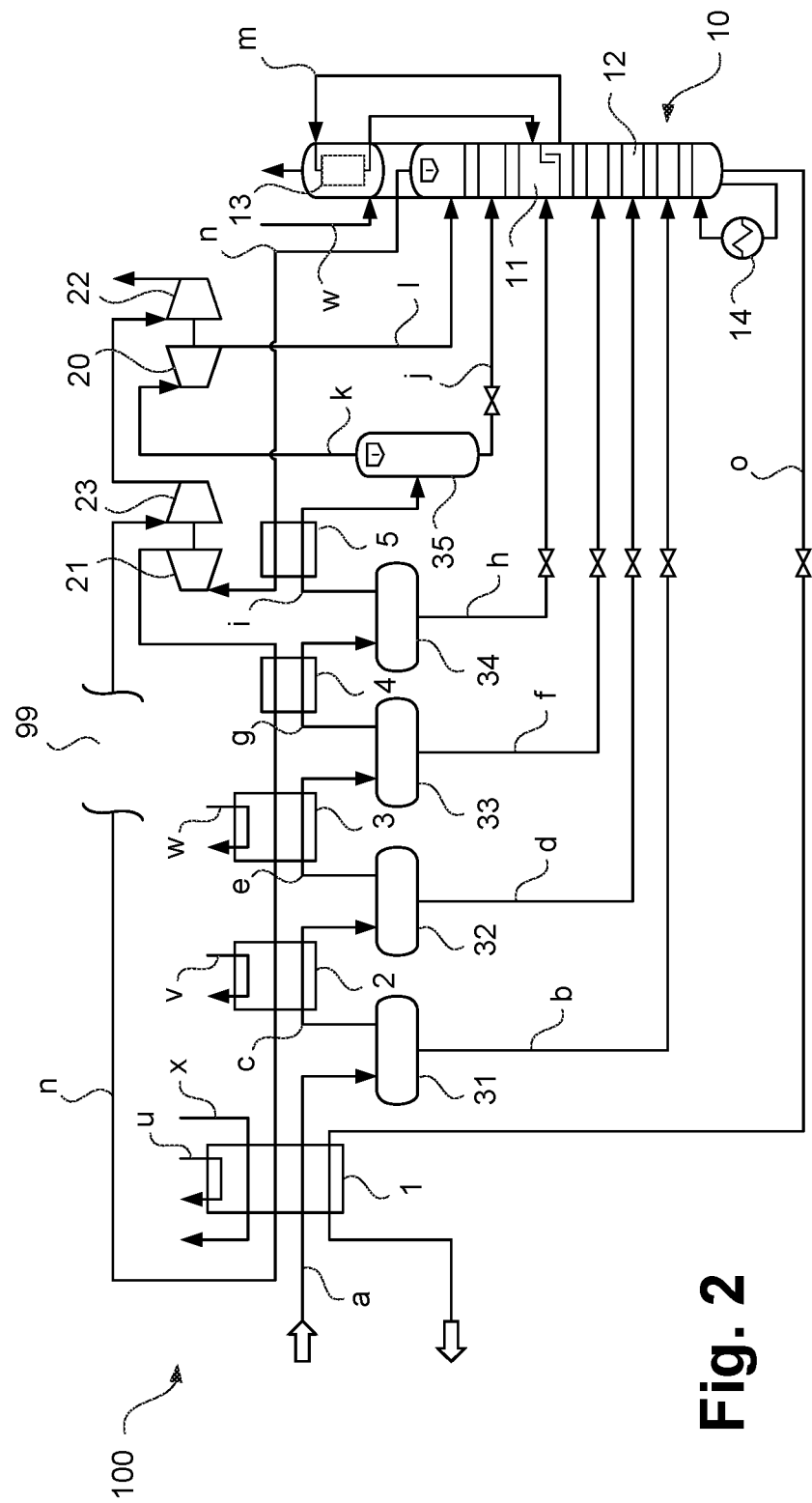
FIG. 2 shows a separation apparatus for separation of a component mixture in one embodiment of the invention.

FIG. 2 shows a separation apparatus 100 in one embodiment of the invention. The separation apparatus 100 comprises the essential components of separation apparatus 200 shown in FIG. 1. These will not be elucidated again.

In separation apparatus 100 as well, a rectification column with two sections is provided. This is referred to hereinafter as distillation apparatus 10. The two sections thereof are referred to hereinafter as first distillation unit 11 and second distillation unit 12. The separation apparatus is assigned a condenser 13. In separation apparatus 100, the first distillation unit 11 is disposed above the second distillation unit 12. The condenser 13 is additionally disposed above the first distillation unit 11. In a departure from the separation apparatus 200 shown in FIG. 1, however, the plate exchangers 15, 16 have been dispensed with here. A stream of matter m corresponding to stream of matter m1 in separation apparatus 100 is cooled by means of ethylene coolant in the condenser 13 and at least partly liquefied. The gaseous stream of matter m is withdrawn from the upper portion of the second distillation unit 12 and fed into the lower portion of the first distillation unit 11. Since the first distillation unit 11 and the second distillation unit 12 are separated from one another by means of a liquid backup tray, the recycled stream of matter m serves for provision of a return stream to the second distillation unit 12. There is no stream of matter here corresponding to stream of matter m2 in separation apparatus 100. A return stream to the first distillation unit 11 is instead provided as elucidated hereinafter.

The successive cooling of the C2minus stream a is extended by a heat exchanger 4 for cooling of a gaseous stream of matter g, and by a heat exchanger 5 for cooling of a gaseous stream of matter i. In addition to the condensates or streams of matter b, d, f and l, condensates or streams of matter h and j are separated out in further liquid separators 34, 35. Fractions that remain in gaseous form in each case are guided through the heat exchangers 4 and 5 in the form of streams of matter g and i and cooled down to the intermediate temperature levels at −120 to −125° C. (stream g) or −140 to −145° C. (stream i). Since stream of matter j has a higher methane and hydrogen content than stream of matter h, and stream of matter h has a higher methane and hydrogen content than stream of matter f, these are fed to distillation apparatus 10 at different heights.

Stream of matter l is formed in separation apparatus 200 in a comparable manner to stream of matter l in separation apparatus 100, but is at a much lower temperature owing to the further cooling in heat exchangers 4 and 5. Owing to the further cooling, it is especially possible to use streams of matter j and l as return stream to the first distillation unit 11. Liquefaction of a stream of matter m2 as in separation apparatus 100 is therefore not required, and so, as mentioned, it is possible to dispense with the heat exchangers 15, 16.

Since, in the present invention, the gaseous stream of matter n which is withdrawn at the top of the distillation apparatus does not have to be used for cooling in the plate exchangers 15, 16, it can be used for cooling in the heat exchangers 1, 2, 3, 4, 5. In this way, the low temperatures mentioned can be achieved.

Figure 3:
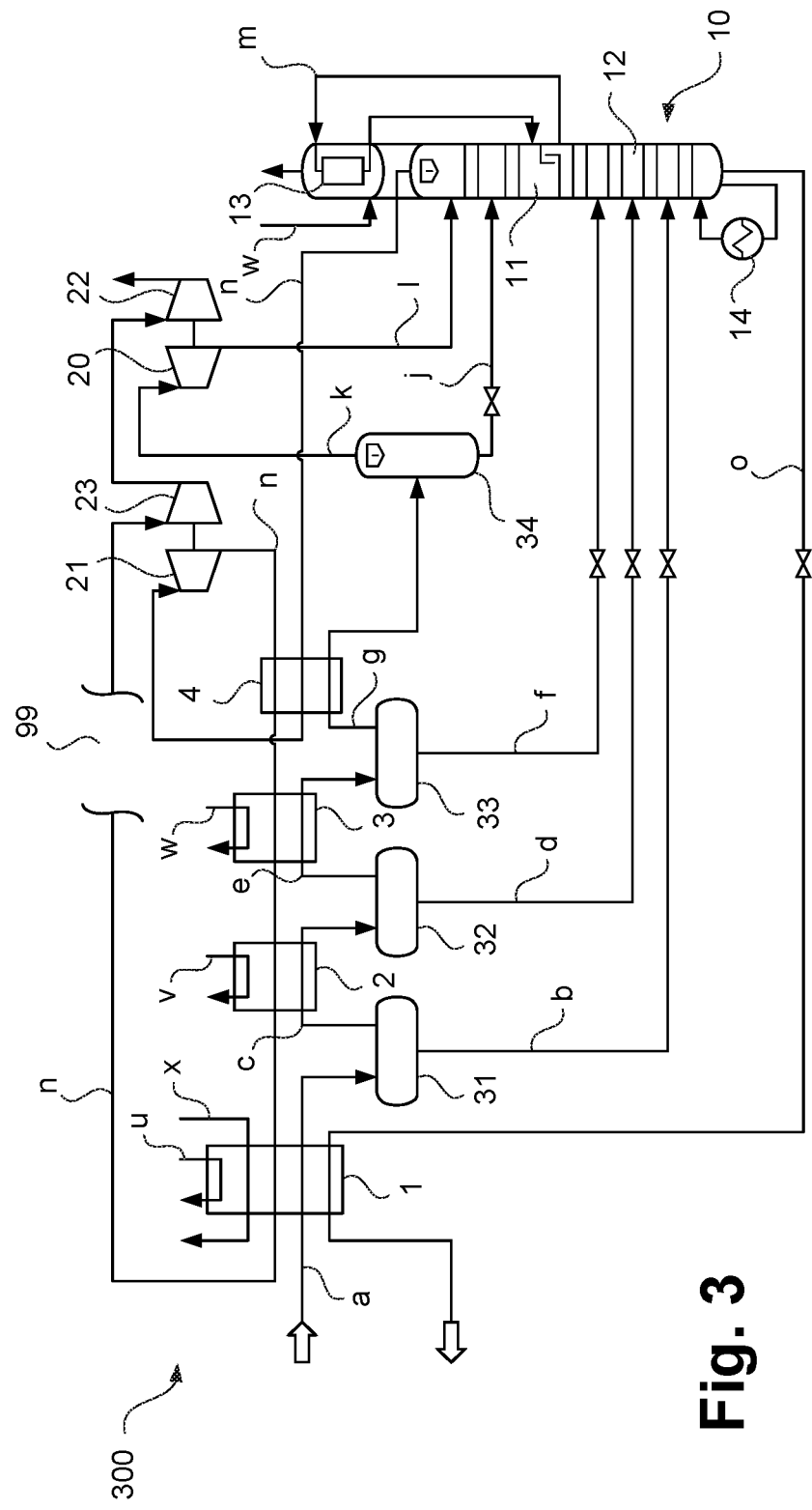
FIG. 3 shows a separation apparatus for separation of a component mixture in a second embodiment of the invention.

FIG. 3 shows a separation apparatus 300 in a further embodiment of the invention. In this case, the separation apparatus according to the prior art has been extended only by a heat exchanger 4 and a liquid separator 34.

In FIGS. 1 to 3, heat exchangers 1 to 3 are each cooled using further streams of matter u, v, w and x. Streams of matter u, v and w are ethylene coolant at different pressure levels; stream of matter x is, for example, a recycled ethane stream. An ethylene coolant stream w through the condenser 13 is correspondingly specified.

Figure 4:
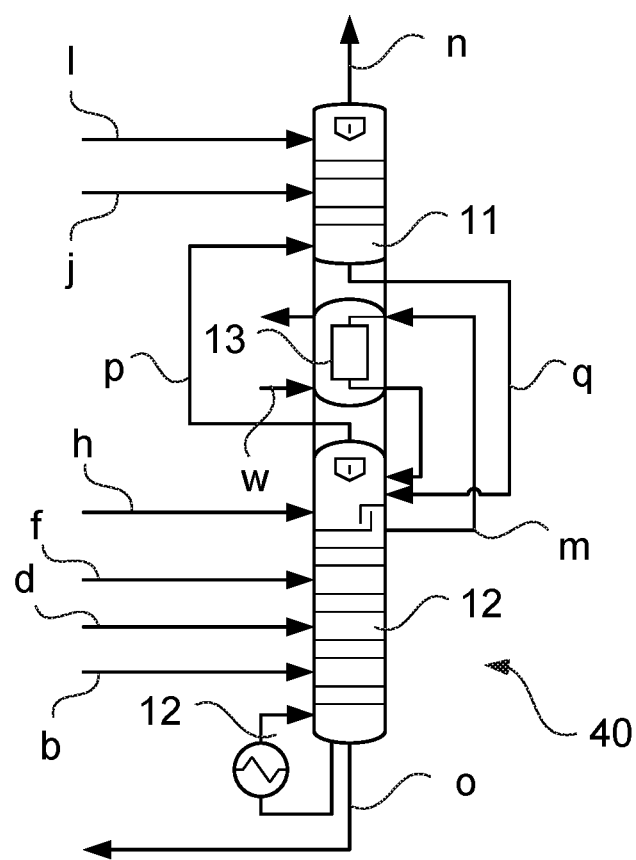
FIG. 4 shows a separation apparatus for separation of a component mixture in a third embodiment of the invention.

FIG. 4 shows the distillation unit 40 in a further embodiment of the invention. In this case, the condenser 13 is disposed between the first distillation unit 11 and the second distillation unit 12, with the first distillation unit 11 disposed above the condenser, and the condenser 13 above the second distillation unit 12. Mass transfer is effected in the form of a stream of matter p and a stream of matter q.

In addition, it would be possible to directly integrate the condenser 13 into the distillation unit 40, for example in the form of a shell-and-tube apparatus or a block between the first distillation unit 11 and the second distillation unit 12. Correspondingly, internals such as the liquid seal would be dispensed with.

The table below gives temperatures of selected streams of matter. The figures in brackets are each preferred temperature ranges; the value after the bracket is a preferred example.

| Separation apparatus | 200 | 100 | 300 |
|---|---|---|---|
| Stream of matter a upstream of heat exchanger 1 | (−25 to −35° C.) −32° C. | (−25 to −35° C.) −32° C. | (−25 to −35° C.) −32° C. |
| Stream of matter a downstream of heat exchanger 1 | (−45 to −55° C.) −51° C. | (−45 to −55° C.) −51° C. | (−45 to −55° C.) −51° C. |
| Stream of matter c downstream of heat exchanger 2 | (−70 to −80° C.) −76° C. | (−74 to −80° C.) −76° C. | (−74 to −80° C.) −76° C. |
| Stream of matter e downstream of heat exchanger 3 | (−95 to −100° C.) −97° C. | (−95 to −100° C.) −97° C. | (−95 to −100° C.) −97° C. |
| Stream of matter g downstream of heat exchanger 4 | | (−115 to −125° C.) −122° C. | (−135 to −145° C.) −143° C. |
| Stream of matter i downstream of heat exchanger 5 | | (−135 to −145° C.) −143° C. | |
| Stream of matter l downstream of expander 20 | (−112 to −118° C.) −115° C. | (−155 to −165° C.) −162° C. | (−155 to −165° C.) −162° C. |
| Stream of matter n after withdrawal | (−150 to −155° C.) −152° C. | (−150 to −155° C.) −153° C. | (−150 to −155° C.) −153° C. |
| Stream of matter o after withdrawal | (−35 to −45° C.) −36° C. | (−35 to −45° C.) −36° C. | (−35 to −45° C.) −36° C. |

The invention claimed is:

1. A process for separating a component mixture (C2minus) comprising essentially hydrocarbons having two or two or more carbon atoms, methane and hydrogen using a distillation apparatus (10), in which
    a first fluid from the component mixture (C2minus) at a first pressure level is cooled down stepwise from a first temperature level via two or more intermediate temperature levels to a second temperature level, with separation of condensates (b, d, f, h, j) out of the first fluid at each of the intermediate temperature levels,
    a second fluid from the component mixture (C2minus) that remains in gaseous form at the second temperature level is cooled down by expanding from the first pressure level to a second pressure level below the first pressure level, forming a biphasic stream (l) comprising a liquid and a gaseous part,
    fluids from the condensates (b, d, f, h, j) and fluid from the biphasic stream (l) is fed into the distillation apparatus (10) which is being operated at the second pressure level, where a liquid stream of matter (o) comprising essentially hydrocarbons having two or two or more carbon atoms and a gaseous stream of matter (n) comprising essentially methane and hydrogen are obtained in the distillation apparatus (10) and are drawn off from the distillation apparatus (10),
characterized in that
    the second temperature level is −125 to −150° C.,
    the distillation apparatus (10) has a first distillation unit (11), a second distillation unit (12), and a condenser (13), wherein the first distillation unit (11) is operated with a third temperature level at its top which is below the second temperature level, the second distillation unit (12) is operated at a fourth temperature level at its top which is below the second temperature level, and the condenser is operated a temperature level above the second temperature level,
    a liquid part of the biphasic stream is at least partially fed into the first distillation unit (11), and
    a gaseous stream of matter (m) is drawn off from the second distillation unit (12) of the distillation apparatus (10), cooled down in the condenser (13) and used to provide a liquid return stream to the second distillation unit (12).

2. The process according to claim 1, wherein the separated condensates (b, d, f, h, j) are fed at least partly into the first and the second distillation units (11, 12) of the distillation apparatus (10).

3. The process according to claim 1, wherein the liquid stream of matter (o) is expanded from the second pressure level to a pressure level below the second pressure level.

4. The process according to claim 1, wherein the first fluid from the component mixture (C2minus) is cooled down using an ethane and/or ethylene coolant at different pressure levels from the first temperature level via the intermediate temperature levels to the second temperature level.

5. The process according to claim 1, wherein the intermediate temperature levels include an intermediate temperature level at −48 to −53° C. and/or an intermediate temperature level at −74 to −79° C. and/or an intermediate temperature level at −95 to −100° C. and/or an intermediate temperature level at −120 to −125° C. and/or an intermediate temperature level at −140 to −145° C.

6. The process according to claim 1, wherein the gaseous stream of matter (m) is cooled down in the condenser (13) by an ethylene coolant.

7. The process according to claim 1, wherein the condenser (13) is disposed between the first distillation unit (11) and the second distillation unit (12).

8. The process according to claim 1, in which fluid from the gaseous stream of matter (n) which is drawn off from the distillation apparatus (10) is used at least to cool down the first fluid from the component mixture (C2minus) from the first temperature level via the intermediate temperature levels to the second temperature level.

9. The process according to claim 1, wherein the fluid from the gaseous stream of matter (n) which is drawn off from the distillation apparatus (10) is expanded in an expander (21) to a third pressure level below the second pressure level.

10. The process according to claim 9, wherein the fluid from the gaseous stream of matter (n) which is drawn off from the distillation apparatus (10), after use for cooling down the first fluid from the component mixture (C2minus), is compressed, using compressors coupled to expanders (20, 21) for compression.

11. The process according to claim 1, which is used for separation of the component mixture (C2minus) which is obtained from a cracked gas obtained by means of a steam cracking process.

12. A process for separating a component mixture (C2minus) comprising essentially hydrocarbons having two or two or more carbon atoms, methane and hydrogen using a distillation apparatus (10), in which
a first fluid from the component mixture (C2minus) at a first pressure level is cooled down stepwise from a first temperature level via two or more intermediate temperature levels to a second temperature level, with separation of condensates (b, d, f, h, j) out of the first fluid at each of the intermediate temperature levels,
a second fluid from the component mixture (C2minus) that remains in gaseous form at the second temperature level is cooled down by expanding from the first pressure level to a second pressure level below the first pressure level, forming a biphasic stream (l) comprising a liquid and a gaseous part,
fluids from the condensates (b, d, f, h, j) and fluid from the biphasic stream (l) is fed into the distillation apparatus (10) which is being operated at the second pressure level, where a liquid stream of matter (o) comprising essentially hydrocarbons having two or two or more carbon atoms and a gaseous stream of matter (n) comprising essentially methane and hydrogen are obtained in the distillation apparatus (10) and are drawn off from the distillation apparatus (10),
characterized in that
the second temperature level is −125 to −150° C.,
the distillation apparatus (10) has a first distillation unit (11), and a second distillation unit (12) wherein the first distillation unit (11) is operated with a third temperature level at its top which is below the second temperature level and the second distillation unit (12) is operated at a fourth temperature level at its top which is below the second temperature level,
a liquid part of the biphasic stream is at least partially fed into the first distillation unit (11), and
the liquid stream of matter (o) is expanded from the second pressure level to a pressure level below the second pressure level.

13. A separation apparatus (100) set up for separation of a component mixture comprising essentially hydrocarbons having two or two or more carbon atoms, methane and hydrogen, wherein the separation apparatus (100) comprises:
one or more indirect heat exchangers (1, 2, 3, 4, 5) which are adapted to cool down a first fluid from the component mixture (C2minus) at a first pressure level stepwise from a first temperature level via two or more intermediate temperature levels to a second temperature level, and one or more liquid separators (31, 32, 33, 34, 35) which are adapted to separate condensates (b, d, f, h, j) out of the first fluid at each of the intermediate temperature levels,
one or more expanders (20) which is or are adapted to cool down a second fluid from the component mixture (C2minus) that remains in gaseous form at the second temperature level by expanding from the first pressure level to a second pressure level below the first pressure level, thereby forming a biphasic stream (l) comprising a liquid part and a gaseous part,
a distillation apparatus (10) and feed lines which are adapted to feed fluid from the condensates (b, d, f, h, j) and fluid from the biphasic stream (l) into the distillation apparatus (10), wherein the distillation apparatus (10) is arranged to operate at the second pressure level and to form a liquid stream of matter (o) comprising essentially hydrocarbons having two carbon atoms and a gaseous stream of matter (n) comprising essentially methane and hydrogen, wherein a withdrawal line is provided which is adapted to draw the gaseous stream of matter (n) off from the distillation apparatus (10),
characterized in that
the distillation apparatus (10) has a first distillation unit (11), a second distillation unit (12), and a condenser (13), wherein the first distillation unit (11) is arranged to be operated at its top with a third temperature level below the second temperature level, the second distillation unit (12) is arranged to be operated at its top at a fourth temperature level above the second temperature level, and the condenser (13) is operated a temperature level above the second temperature level,
a reflux line is provided which is adapted to feed a liquid part of the biphasic stream at least partially as a reflux to the first distillation unit (11), and
a gaseous stream of matter (m) is drawn off from the second distillation unit (12) of the distillation apparatus (10), cooled down in the condenser (13) and used to provide a liquid return stream to the second distillation unit (12).

* * * * *